United States Patent [19]

Murayama

[11] Patent Number: 5,401,503
[45] Date of Patent: Mar. 28, 1995

[54] HAIR GROWTH STIMULANT

[75] Inventor: Mitsuo Murayama, Utsunomiya, Japan

[73] Assignee: Sanwa Shoyaku Kabushiki Kaisha, Tochigi, Japan

[21] Appl. No.: 140,002
[22] PCT Filed: Feb. 9, 1993
[86] PCT No.: PCT/JP93/00164
    § 371 Date: Oct. 25, 1993
    § 102(e) Date: Oct. 25, 1993
[87] PCT Pub. No.: WO93/17657
    PCT Pub. Date: Sep. 16, 1993

[30] Foreign Application Priority Data
    Mar. 12, 1992 [JP] Japan .................. 4-103434
    Apr. 7, 1992 [JP] Japan .................. 4-129235

[51] Int. Cl.⁶ ............................. A61L 35/78
[52] U.S. Cl. ................... 424/195.1; 424/70.1; 424/74; 514/929
[58] Field of Search ............ 424/195.1, 70, 74; 514/929

[56] References Cited

U.S. PATENT DOCUMENTS 4,352,792 10/1982 Arichi et al. ................ 429/195.1

FOREIGN PATENT DOCUMENTS 63-234014 10/1987 Japan ............. A61K 7/50
3-271213 12/1991 Japan ............. A61K 7/06

*Primary Examiner*—John W. Rollins
*Attorney, Agent, or Firm*—Nixon & Vanderhye

[57] ABSTRACT

A composition for use in hair growth stimulant and blood circulation stimulant, which contains as active ingredient an extract fraction containing non-aconitine type alkaloidal components which is obtained by extracting Aconitum roots with water or alcohol and removing aconitine type alkaloidal components from the resultant aqueous or alcoholic extract.

8 Claims, No Drawings

HAIR GROWTH STIMULANT

FIELD OF THE INVENTION

The present invention relates to a composition for hair growth stimulant and/or blood circulation stimulant, which is characterized in that the extract fraction of Aconitum roots containing non-aconitine type alkaloidal components is used as active ingredient.

BACKGROUND ART

Alopecia is known to be caused, for example, by the reduction of the physiological function of the scalp due to nourishment imbalance or excessive production of dandruff, by the reduction of metabolism in the hair papilla due to insufficient blood supply thereto resulting from the reduction of peripheral blood flow, by the androgen-associated reduction of the hair follicle's function in the sebaceous gland, hair follicle or hair-root, or by psychic stress, and a variety of drugs are used for the treatment of alopecia or the like. Examples of such drugs include ethinylestradiol showing anti-androgenic activity; vitamin E, swertiae herba extract, carrot extract, cepharanthin or the like showing peripheral blood flow stimulating activity; and capsicum tincture, peppermint oil, menthol or the like showing local stimulative activity. There are, however, no satisfactory drugs as yet.

The present inventor has previously provided "hair growth stimulant characterized by containing aqueous or alcoholic extract of Aconitum roots, stems or leaves" (Japanese published unexamined patent application No. 3-271213 (JP, A, 3-271213). As a result of further studies on the aqueous or alcoholic extract of Aconitum roots, the present inventor has found that the extract fraction of Aconitum roots containing non-aconitine type alkaloidal components has an extremely remarkable stimulative action on hair growth and hair growing as compared to simple aqueous or alcoholic extract of Aconitum roots, and also that this fraction is significantly superior thereto in respect of safety when used in human beings. The present invention has been achieved based on these findings.

It has not hitherto been known that non-aconitine type alkaloidal components have a stimulative action on hair growth and hair growing. The present invention thus provides a novel hair growth stimulant characterized by using as active ingredient the extract fraction of Aconitum roots containing non-aconitine type alkaloidal components.

The present inventor has also found that the above-mentioned fraction of Aconitum roots containing non-aconitine type alkaloidal components has a remarkable peripheral blood flow-increasing action.

It has not hitherto been known that non-aconitine type alkaloidal components has a blood flow-increasing action. Accordingly the present invention further provides a novel pharmaceutical for blood circulation stimulation characterized by using the extract fraction of Aconitum roots containing non-aconitine type alkaloidal components.

DISCLOSURE OF THE INVENTION

According to the present invention there is provided a hair growth stimulant, characterized in that an extract fraction of Aconitum roots is used as active ingredient which is obtained by extracting the roots with water or alcohol and separating the resultant aqueous or alcoholic extract by means of mass partition between solid-liquid phases or liquid-liquid phases to remove aconitine-type alkaloidal components.

According to the present invention, there is also provided a pharmaceutical for blood circulation stimulation characterized by using said extract fraction as active ingredient.

The present invention will now be described in detail in the following.

The raw materials, Aconitum roots, used in the present invention are roots of plants of the genus Aconitum which belongs to the family Ranunclaceae. As major species there may be mentioned *Aconitum japonicum* $T_{HUNB}$, *Aconitum subcuneatum* $N_{AKAI}$, *Aconitum japonicum* $T_{HUNB}$. var. montanum, *Aconitum carmichaeli* $D_{EBX}$. and *Aconitum yesoense* $N_{AKAI}$. In addition to these a number of other species are also known as plants of the genus Aconitum. The raw material used in the present invention is appropriately chosen from these species belonging to the genus Aconitum.

In the process for the preparation of the extract fraction used as active ingredient in the hair growth stimulant or blood circulation stimulant of the present invention, Aconitum roots are, preferably after finely divided, mixed with water or alcohol such as methanol or ethanol to effect extraction at room temperature or under heating and the resultant aqueous or alcoholic extract is separated by means of mass partition between solid-liquid phases or liquid-liquid phases to remove aconitine type alkaloidal components, whereby the extract fraction containing non-aconitine type alkaloidal components is obtained.

Since Aconitum roots generally contain extremely poisonous alkaloids, aqueous or alcoholic extracts thereof require special attention in their handling. From that standpoint of view, it is preferred to use Aconitum roots which have been subjected to attenuation treatment, for example by heating. As examples of such treatment, there may be mentioned (1) heating Aconitum roots under pressure in an autoclave; (2) steaming them in a steaming cage; and (3) cooking them in a pot.

In carrying out the extraction from Aconitum roots, water and alcohol may be used, either alone or in combination, as extraction solvent. As the alcohol for this purpose, it is preferred to choose methanol or ethanol. Where alcohol is used to effect extraction under heating, it is preferably performed by means of refluxing. The extraction may be carried out under stirring with a stirrer, wherein ultrasonic waves are preferably applied.

As means for the separation by means of mass partition or differentiated mass adsorption between two phases such as solid-liquid phases or liquid-liquid phases, there may be mentioned, for example, varied chromatography such as adsorption chromatography, ion-exchange chromatography or partition chromatography. Furthermore, gel filtration or the like method, which is a means for fractionating materials on the basis of differences in molecular size, may also be used for this purpose of separation. The above-mentioned water or alcohol extract can be treated by using these ways and means to remove aconitine-type alkaloidal components and thereby to afford the extract fraction containing non-aconitine type alkaloidal components.

In carrying out the above-mentioned adsorption chromatography, adsorbents in conventional use for column chromatography, such as polyamide, activated charcoal, activated silica gel, activated alumina or the like support, may be used.

Where polyamide is used as the support, the desired extract fraction containing non-aconitine type alkaloidal can be obtained by the following procedure: The extract of Aconitum roots with water or alcohol, as such in the case of the aqueous extract or in the form, in the case of the alcoholic extract, of a suspension of its concentrated-to-dryness product in water, is loaded onto a column packed with polyamide so that the extracted components are adsorbed thereon. The column is then washed with water to remove aconitine-type alkaloidal components and subsequently eluted with an appropriate solvent such as ethanol made alkaline with ammonia to give the desired extract fraction.

Where activated charcoal is used as the support, the extract of Aconitum roots with water or alcohol, as such in the case of aqueous extract or in the form, in the case of the alcoholic extract, of a suspension of its concentrated-to-dryness product in water, is loaded onto a column packed with activated charcoal for adsorption. The column is washed with an appropriate solvent such as 20% methanol and then eluted with an appropriate solvent such as methanol made alkaline with ammonia to give the desired extract fraction containing non-aconitine type alkaloidal components.

Where silica gel is used as the support, the extract of Aconitum roots with water or alcohol is concentrated to dryness and the resultant aqueous or alcoholic extract is suspended in a small volume of methanol. The suspension is loaded onto a column packed with silica gel for adsorption. The column is washed with an appropriate solvent mixture such as chloroform/methanol/ammonia water (50:10:1) to remove aconitine type alkaloidal components and then eluted with an appropriate solvent mixture such as chloroform/methanol/water (6:4:1) to give the desired extract fraction containing non-aconitine type alkaloidal components.

Where alumina is used as the support, the extract from Aconitum roots with water or alcohol is concentrated to dryness and the resultant aqueous or alcoholic extract is suspended in a small volume of methanol. The suspension is loaded onto a column packed with alumina for adsorption. The column is washed with an appropriate solvent mixture such as chloroform/methanol (4:1) to remove aconitine type alkaloidal components and then eluted with an appropriate solvent mixture such as chloroform/methanol/water (12:10:3) to give the desired extract fraction containing non-aconitine type alkaloidal components.

The afore-mentioned ion-exchange chromatography can be performed with the use of different ion exchangers such as ion-exchange resin, ion-exchange cellulose or ion-exchange dextran. For example, where CM-Sephadex C-25, an ion-exchange dextran, is used, the desired extract fraction containing non-aconitine alkaloidal components can be obtained by the following procedure: The extract of Aconitum roots with water or alcohol, as such in the case of the aqueous extract or in the form, in the case of the alcoholic extract, of a suspension of its concentrated-to-dryness product in water, is loaded onto a column packed with CM-Sephadex C-25 so that the extracted components are absorbed thereon. The column is then eluted with water to give the desired extract fraction.

When column chromatography is used to perform the afore-mentioned partition chromatography, there may be used different solid phase-supporting materials such as silica gel or Sephadex. For example, where CM-Sephadex C-25 is used as the solid phase-supporting material, the extract of Aconitum roots with water or alcohol, as such in the case of the aqueous extract or in the form, in the case of the alcoholic extract, of its concentrated-to-dryness product in water, is loaded onto a column packed with CM-Sephadex C-25 and the column is then eluted with water to give the desired extract fraction containing non-aconitine type alkaloidal components. Where the partition is effected with the use of an aqueous-organic solvent system, there may be used, for example, an acidic or alkaline aqueous solution as the aqueous solvent system, and ether or n-butanol as the organic solvent system. Thus, for example, the extract of Aconitum roots with water or alcohol is concentrated to dryness and the resultant aqueous or alcoholic extract is dissolved in 1N ammonia water. The solution is washed with ether and the aqueous phase is made acidic with hydrochloric acid and then extracted with n-butanol. The n-butanolic extract is washed with hydrochloric acid to give the desired extract fraction containing non-aconitine type alkaloidal components.

In the afore-mentioned gel filtration, appropriate gel particles of network structure may be used as support. Thus, for example, where commercially available Toyopearl HW 40F is used, the extract of Aconitum roots with water or alcohol is concentrated to dryness and the resultant aqueous or alcoholic extract is suspended in an appropriate solvent such as 50% methanol. The suspension is loaded onto a column packed with Toyopearl HW 40F and the column is washed with an appropriate quantity of 50% methanol and then eluted with 50% methanol to give the desired extract fraction containing non-aconitine type alkaloidal components.

The extract fraction containing non-aconitine type alkaloidal components obtained from Aconitum roots used in the present invention is diluted, either as such, i.e. in the form of liquid, or after concentrated to dryness, in an appropriate base before its application. As such base there may be used carriers and additives such as emulsifying agents, suspending agents and perfume agents, which are customarily used as appropriate or necessary in the art of cosmetics, pharmaceuticals, etc. The extract fraction of the invention can be processed by conventional methods into preparations for application. Examples of materials for such base include oleic acid, triethanolamine, white beeswax, cetyl alcohol, sodium lauryl sulfate, glycerin, sodium alginate, gum arabic, sodium carboxymethyl cellulose, methyl cellulose, bentonite, vaseline, liquid paraffin, alcohols and esters thereof such as ethanol, propylene glycol, cetostearyl alcohol and sorbitan monostearate. These preparations may be presented in different application forms such as hair tonic, hair cream, hair lotion and hair shampoo.

Preparations for topical application are presented, for example, in the form of compositions for ointment, plaster or poultice or of toning lotion or cream. They may contain those carriers well known in the art such as vaseline, paraffin, hydrous lanolin, plastibase, kaolin, bentonite, talc, aluminum silicate, propylene glycol, sorbitol, hydrophilic petrolatum, macrogols, wax, resin, purified lanolin, gum, glycerin, gelatin, polyacrylic acid, polyacrylic acid salt, polyvinyl alcohol, polyvinyl pyrrolidone, polyethylene oxide, beeswax, cacao butter, carnauba wax, stearyl alcohol, olive oil, castor oil, ethanol, oleic acid, cetyl alcohol, gum arabic, sodium alginate, carboxymethyl cellulose and methyl cellulose.

The content as dry concentrate of the extract fraction containing non-aconitine type alkaloidal components of Aconitum roots in the above preparation is about 0.05–10%, preferably 0.1–5%.

The blood circulation stimulant according to the present invention may take forms for oral administration such as tablets, powders, granules and capsules or those for rectal administration. In the case of these forms the clinical dose for adults of the extract fraction containing non-aconitine type alkaloidal components of Aconitum roots is, as dry concentrate thereof, 10–1000 mg/day, preferably 100–600 mg/day.

Oral preparations such as tablets, powders, granules and capsules may contain conventional excipients such as calcium carbonate, magnesium carbonate, calcium phosphate, corn starch, potato starch, sugar, lactose, talc, magnesium stearate and gum arabic. Tablets may be coated by conventional methods. Oral liquid preparations may be aqueous or oily suspensions, solutions, syrups, elixirs etc.

Preparations for rectal administration may be presented in the form of compositions for suppository and may contain carriers well known in the art such as polyethylene glycol, lanolin and coconut oil.

Preparations for injection may contain different adjuvants such as suspending, stabilizing or dispersing agents. Thus, for example, they may contain sterilized distilled water, refined oils such as peanut oil or corn oil, non-aqueous solvents, polyethylene glycol, polypropylene glycol etc.

In the following will now be given working examples of preparation of the extract fraction containing non-aconitine type alkaloidal components in accordance with the present invention, as well as purity tests (for presence of aconitine type alkaloids), pharmacological tests, safety tests and examples of formulation.

EXAMPLE 1

① Aconitum roots were autoclaved at 110° C. for 40 min., dried and then ground.

② 4 l of methanol was added to 1 kg of the obtained coarse powder and extraction was effected by refluxing for 30 min under heating on a water bath. After extraction, the mixture was allowed to stand and the supernatant was filtered. To the residue, 4 l of methanol was added and, the extraction operation of reflux under heating was repeated as described above. The obtained filtrate was combined with the previously obtained filtrate. The filtrate was concentrated to dryness to afford 100 of methanolic extract.

3. 18 g of the methanolic extract was suspended in 10 ml of water, and the suspension was then loaded onto a column packed with 75 g of polyamide so that the extracted components were adsorbed thereon. This column was washed with 1 l of water and then eluted with 1 l of ethanol made alkaline with 3% ammonia. The eluate was concentrated to dryness under reduced pressure to afford 1.8 g of dry concentrate of the extract fraction containing non-aconitine type alkaloidal components.

Purity Test 10 mg of the extract fraction containing non-aconitine type alkaloidal components obtained by the above-mentioned procedure was dissolved in 1 ml of methanol. After 0.5 g of polyamide was added to this solution and the mixture thoroughly stirred, the methanol was distilled off. The residue was loaded onto a column packed with 2 g of polyamide and this column was eluted with 40 ml of water. The eluate was concentrated to dryness under reduced pressure. The obtained residue was dissolved in 1 ml of methanol to give a sample solution. 3 $\mu$l of the sample solution was spotted on a thin layer plate prepared with silica gel for thin layer chromatography. The plate was then developed with ammonia-saturated chloroform/methanol (15:1) as a developing solvent and was then air-dried. To this plate, Dragendorff reagent (note was uniformly sprayed. No orange color spots were found.

(note 1) It was prepared by adding 2 ml of a solution prepared by dissolving 8 g of potassium iodide in 20 ml of water and 20 ml of 20% acetic acid solution to 2 ml of a solution prepared by dissolving 0.85 g of bismuth subnitrate in 10 ml of glacial acetic acid.

Experiments on Added Standard Substance Recovery in the Abovementioned Purity Test

Experiment 1

Full test: About 3 mg of aconitine was so weighed to give a precise weight (a) and was dissolved in 1 ml of methanol. After 0.5 g of polyamide was added to this solution and the mixture thoroughly stirred, the methanol was distilled off. The residue was loaded onto a column packed with 2 g of polyamide. The column was then eluted with 40 ml of water. After the eluate was concentrated to dryness, the weight of the residue (b) was measured.

Blank test: The weight of the residue (c) was measured in the same manner as in the above-mentioned full test, except for the use of 1 ml of methanol as a substitute for 1 ml of the methanolic solution of aconitine in the above-mentioned full test.

On each of mesaconitine, hypaconitine and jesaconitine, the same tests as on aconitine were performed. Each test was repeated three times for each standard substance. The results are shown in the following Table 1. In Table 1, "weight of recovered standard substance" and "recovery percentage" were calculated from the following equations.

(weight of recovered standard substance) = $b - c$ (recovery percentage) = $(b-c) \times 100/a$

TABLE 1

| Aconitine type alkaloids | | weight of standard substance loaded onto column (mg) | weight of recovered standard substance (mg) | recovery percentage (%) | relative standard deviation (%) |
| --- | --- | --- | --- | --- | --- |
| aconitine | 1 | 3.01 | 2.96 | 98.3 | 0.59 |
| | 2 | 2.96 | 2.94 | 99.3 | |
| | 3 | 2.99 | 2.94 | 98.3 | |
| mesaconitine | 1 | 3.08 | 3.05 | 99.0 | 0.56 |
| | 2 | 3.10 | 3.08 | 99.4 | |
| | 3 | 3.02 | 2.97 | 98.3 | |
| hypaconitine | 1 | 3.11 | 3.04 | 97.7 | 0.52 |

TABLE 1-continued

| Aconitine type alkaloids | | weight of standard substance loaded onto column (mg) | weight of recovered standard substance (mg) | recovery percentage (%) | relative standard deviation (%) |
| --- | --- | --- | --- | --- | --- |
| | 2 | 3.04 | 3.00 | 98.7 | |
| | 3 | 3.09 | 3.04 | 98.4 | |
| jesaconitine | 1 | 2.95 | 2.94 | 99.7 | 0.41 |
| | 2 | 3.06 | 3.03 | 99.0 | |
| | 3 | 3.13 | 3.10 | 99.0 | |

Experiment 2

Full test: 20 mg of the extract fraction containing non-aconitine type alkaloidal components obtained in Example 1 mentioned above was dissolved in 2 ml of methanol. 1 ml of this solution was named as solution A and the remaining 1 ml as solution B. About 3 mg of aconitine was so weighed as to give precise weight (a) and was dissolved in solution A. After 0.5 g of polyamide was added to this solution and the mixture thoroughly stirred, the methanol was distilled off and the residue was loaded onto a column packed with 2 g of polyamide. The column was then eluted with 40 ml of water. After the eluate was concentrated to dryness, the weight of the residue (b) was measured.

Blank test: The weight of the residue (c) was measured in the same manner as in the above-mentioned full test, except for the use of solution B as a substitute for solution A having aconitine dissolved therein.

On each of mesaconitine, hypaconitine and jesaconitine, the same tests as on aconitine were performed. Each test was repeated three times for each standard substance. The results are shown in the following Table 2. In Table 2, "weight of recovered standard substance" and "recovery percentage" were calculated from the following equations.

$$(\text{weight of recovered standard substance}) = b - c$$

$$(\text{recovery percentage}) = (b - c) \times 100/a$$

10 ml of water, it was adsorbed on a column packed with 20 g of activated charcoal. The column was then washed with 600 ml of 20% methanol and subsequently eluted with 600 ml of methanol made alkaline with ammonia. The eluate was concentrated to dryness under reduced pressure to give 786 mg of dry concentrate of the extract fraction containing non-aconitine type alkaloidal components.

Purity Test

The same procedure as in the purity test described in Example 1 was followed to find no orange color spots.

EXAMPLE 3

Methanolic extract was obtained by following the same procedure as in ①  and ② described in Example 1. After 4 g of the methanolic extract was suspended in 100 ml of in 1N ammonia water, the suspension was washed 5 times with 100 ml of ether. To the aqueous layer, 17 ml of 10N hydrochloric acid was added and the mixture was extracted 2 times with 100 ml of n-butanol. After the extract was washed 5 times with 20 ml of 1N hydrochloric acid, it was concentrated to dryness under reduced pressure to give 424 mg of dry concentrate of the fraction containing non-aconitine type alkaloidal components.

Purity Test

The same procedure as in the purity test described in Example 1 was followed to find no orange color spots.

TABLE 2

| Aconitine type alkaloids | | weight of standard substance loaded onto column (mg) | weight of recovered standard substance (mg) | recovery percentage (%) | relative standard deviation (%) |
| --- | --- | --- | --- | --- | --- |
| aconitine | 1 | 3.24 | 3.21 | 99.1 | 0.36 |
| | 2 | 3.12 | 3.07 | 98.4 | |
| | 3 | 3.18 | 3.14 | 98.7 | |
| mesaconitine | 1 | 2.86 | 2.80 | 97.9 | 0.47 |
| | 2 | 3.12 | 3.08 | 98.7 | |
| | 3 | 3.10 | 3.06 | 98.7 | |
| hypaconitine | 1 | 2.92 | 2.85 | 97.6 | 0.54 |
| | 2 | 3.06 | 3.01 | 98.4 | |
| | 3 | 2.88 | 2.84 | 98.6 | |
| jesaconitine | 1 | 3.24 | 3.21 | 99.1 | 0.21 |
| | 2 | 3.09 | 3.06 | 99.0 | |
| | 3 | 3.03 | 2.99 | 98.7 | |

From the results of (experiment 1) and (experiment 2), it was confirmed that high recovery percentages of aconitine type alkaloids were obtained in this purity test and also that this purity test was highly reproducible as evidenced by the values of relative standard deviation. In the following examples, the purity test was performed in accordance with the same method as the mentioned above.

EXAMPLE 2

Methanolic extract was obtained by following the same procedure as in ① and ② described in Example 1. After 4 g of the methanolic extract was suspended in

EXAMPLE 4

Methanolic extract was obtained by following the same procedure as in ① and ② described in Example 1. After 0.9 g of the methanolic extract was suspended in 5 ml of water, the suspension as loaded onto a column packed with 45 g of CM-Sephadex C-25 (Pharmacia Fine Chemicals) so that the extracted components were adsorbed thereon. The column was eluted with 450 ml of water and the obtained extract fraction was concentrated to dryness under reduced pressure to give 630 mg of dry concentrate of the extract fraction containing non-aconitine type alkaloidal components.

Purity Test

The same procedure as in the purity test described in Example 1 was followed to find no orange color spots.

EXAMPLE 5

Methanolic extract was obtained by following the same procedure as in ① and ② described in Example 1. 1 g of the methanolic extract was suspended in 1 ml of methanol and the suspension was loaded onto a column packed with 100 g of alumina so that the extracted components were adsorbed thereon. The column was then washed with 400 ml of chloroform/methanol (4:1) and was eluted with 300 ml of chloroform/methanol/water (12:10:3). The eluate was concentrated to dryness under reduced pressure to give 60 mg of dry concentrate of the extract fraction containing non-aconitine type alkaloidal components.

Purity Test

The same procedure as in the purity test described in Example 1 was followed to find no orange color spots.

EXAMPLE 6

Methanolic extract was obtained by following the same procedure as in ① and ② described in Example 1. After 0.2 g of the methanolic extract was suspended in 0.5 ml of methanol, the suspension was loaded onto a column packed with 20 g of silica gel so that the extracted components were adsorbed thereon. The column was then washed with 300 ml of chloroform/methanol/ammonia (50:10:1) and subsequently eluted with 150 ml of chloroform/methanol/water (6:4:1). The obtained extract fraction was concentrated to dryness under reduced pressure to give 42 mg of dry concentrate of the extract fraction containing non-aconitine type alkaloidal components.

Purity Test

The same procedure as in the purity test described in Example 1 was followed to find no orange color spots.

EXAMPLE 7

Methanolic extract was obtained by following the same procedure as in ① and ② described in Example 1. After 0.38 g of the methanolic extract was suspended in 0.5 ml of 50% methanol, the suspension was loaded onto a column packed with 70 ml of Toyopearl H 40 F. The column was then washed with 45 ml of 50% methanol and subsequently eluted with 120 ml of 50% methanol. The obtained extract fraction was concentrated to dryness under reduced pressure to give 228 ml of dry concentrate of the extract fraction containing non-aconitine type alkaloidal components.

Purity Test

The same procedure as in the purity test described in Example 1 was followed to find no orange color spots.

EXAMPLE 8

① 4 l of methanol was added to 1 kg of finely divided Aconitum roots and the mixture was extracted for 30 min by refluxing under heating. After extraction, it was allowed to stand and the supernatant was filtered. To the residue, 4 l of methanol was added and the same extraction operation as described above was repeated. The obtained filtrate was combined with the previously obtained one and concentrated to dryness under reduced pressure to give 150 g of methanolic extract.

② After 16 g of the obtained methanolic extract was suspended in 10 ml of water, this suspension was loaded onto a column packed with 75 g of polyamide so that the extract components were adsorbed thereon. This column was washed with 1 l of water and then eluted with 1 l of ethanol made alkaline with 3% ammonia. The eluate was concentrated to dryness under reduced pressure to give 1.8 g of dry concentrate of the extract fraction containing non-aconitine type alkaloidal components.

Purity Test

The same procedure as in the purity test described in Example 1 was followed to find no orange color spots.

EXAMPLE 9

Methanolic extract was obtained by following the same extraction procedure as in Example 8 ①. After 4 g of the methanolic extract was suspended in 10 ml of water, the mixture was loaded onto a column packed with 20 g of activated charcoal so that the extracted components were adsorbed thereon. The column was then washed with 600 ml of 20% methanol and subsequently eluted with 600 ml of 20% methanol made alkaline with ammonia. The eluate was concentrated to dryness under reduced pressure to give 770 mg of dry concentrate of the extract fraction containing non-aconitine type alkaloidal components.

Purity Test

The same procedure as in the purity test described in Example 1 was followed to find no orange color spots.

EXAMPLE 10

Methanolic extract was obtained by following the same procedure as in Example 8 ①. After 4 g of the methanolic extract was suspended in 100 ml of 1N ammonia water, the suspension was washed 5 times with 100 ml of ether. To the aqueous layer, 17 ml of 10N hydrochloric acid was added and the mixture was extracted 2 times with 100 ml of n-butanol. After the extract was washed 5 times with 20 ml of 1N hydrochloric acid, it was concentrated to dryness under reduced pressure to give 421 mg of dry concentrate of the extract fraction containing non-aconitine type alkaloidal components.

Purity Test

The same procedure as in the purity test described in Example 1 was followed to find no orange color spots.

EXAMPLE 11

Methanolic extract was obtained by following the same extraction as in Example 8 ①. After 0.9 g of the methanolic extract was suspended in 5 ml of water, it was loaded onto a column packed with 45 g of CM-Sephadex C-25 (Pharmacia Fine Chemicals) so that the extracted components were adsorbed thereon. The column was then eluted with 450 ml of water and the obtained fraction was concentrated to dryness under reduced pressure to give 625 mg of dry concentrate of the extract fraction containing non-aconitine type alkaloidal components.

Purity Test

The same procedure as in the purity test described in Example 1 was followed to find no orange color spots.

EXAMPLE 12

Methanolic extract was obtained by following the same extraction procedure as in Example 8 ①. 1 g of the methanolic extract was suspended in 1 ml of methanol and was loaded onto a column packed with 100 g of alumina so that the extracted components were adsorbed thereon. The column was then washed with 400 ml of chloroform/methanol (4:1) and subsequently eluted with 300 ml of chloroform/methanol/water (12:10:3). The eluate was concentrated to dryness under reduced pressure to give 2 mg of dry concentrate of the extract fraction containing non-aconitine type alkaloidal components.

Purity Test

The same procedure as in the purity test described in Example 1 was followed to find no orange color spots.

EXAMPLE 13

Methanolic extract was obtained by following the same extraction procedure as in Example 8 ①. After 0.2 g of the methanolic extract was suspended in 0.5 ml of methanol, it was loaded onto a column packed with 20 g of silica gel so that the extracted components were adsorbed thereon. The column was then washed with 300 ml of chloroform/methanol/ammonia water (50:10:1) and subsequently eluted with 150 ml of chloroform/methanol/water (6:4:1). The obtained fraction was concentrated to dryness under reduced pressure to give 44 mg of dry concentrate of the extract fraction containing non-aconitine type alkaloidal components.

Purity Test

The same procedure as in the purity test described in Example 1 was followed to find no orange color spots.

EXAMPLE 14

Methanolic extract was obtained by following the same extraction procedure as in Example 8 ①. After 0.38 g of the methanolic extract was suspended in 0.5 ml of 50% methanol, it was loaded onto a column packed with 70 ml of Toyopearl HW 40 F so that the extracted components were adsorbed thereon. The column was then washed with 45 ml of 50% methanol and subsequently eluted With 120 ml of 50% methanol. The obtained fraction was concentrated to dryness under reduced pressure to give 230 mg of dry concentrate of the extract fraction containing non-aconitine type alkaloidal components.

Purity Test

The same procedure as in the purity test described in Example 1 was followed to find no orange color spots.

EXAMPLE 15

Aconitum roots were autoclaved at 110° C. for 40 min., dried and then ground. To 100 g of the obtained coarse powder, 1 l of water was added to effect extraction under heating at about 100° C. for 1.5 hours. After the extract was allowed to cool at room temperature, it was centrifuged. The supernatant was loaded onto a column packed with 150 g of polyamide so that the extracted components were adsorbed thereon. The column was then washed with 2 l of water and subsequently eluted with 2 l of ethanol made alkaline with 3% ammonia. The eluate was concentrated to dryness under reduced pressure to give 1.5 g of dry concentrate of tile extract fraction containing non-aconitine type alkaloidal components.

Purity Test

The same procedure as in the purity test described in Example 1 was followed to find no orange color spots.

EXAMPLE 16

Aconitum roots were autoclaved at 110° C. for 40 min., dried and then ground. To 100 g of the obtained coarse powder, 1 l of water was added to effect extraction under heating at about 100° C. for 1.5 hours. After the extract was allowed to cool at room temperature, it was centrifuged. The supernatant was loaded onto a column packed with 150 g of activated charcoal so that the extracted components were adsorbed thereon. The column was then washed with 5 l of 20% methanol and subsequently eluted with 4.5 l of methanol made alkaline with 3% ammonia. The eluate as concentrated to dryness under reduced pressure to give 2.8 g of dry concentrate of the extract fraction containing non-aconitine type alkaloidal components.

Purity Test

The same procedure as in the purity test described in Example 1 was followed to find no orange color spots.

EXAMPLE 17

① Aconitum roots were autoclaved at 110° C. for 40 min., dried and then ground. To 100 g of the obtained coarse powder, 1 l of water was added to effect extraction under heating at about 100° C. for 1.5 hours. After the extract was allowed to cool at room temperature, it was centrifuged. The supernatant was concentrated to dryness under reduced pressure to give aqueous extract.

After 4 g of the aqueous extract was suspended in 100 ml of 1N ammonia water, it was washed 5 times with 100 ml of ether. To the aqueous layer, 17 ml of 10N hydrochloric acid was added and the mixture was extracted 2 times with 100 ml of n-butanol. After the extract was washed 5 times with 20 ml of 1N hydrochloric acid, it was concentrated to dryness under reduced pressure to give 200 mg of dry concentrate of the extract fraction containing non-aconitine type alkaloidal components.

Purity Test

The same procedure as in the purity test described in Example 1 was followed to find no orange color spots.

EXAMPLE 18

Aconitum roots were autoclaved at 110° C. for 40 min., dried and then ground. To 100 g of the obtained coarse powder, 1 l of water was added to effect extraction under heating at about 100° C. for 1.5 hours. After the extract was allowed to cool at room temperature, it was centrifuged. The volume of the supernatant was made up to 1 l with water and 100 ml of this solution was loaded onto a column packed with 80 g of CM-Sephadex C-25 (Pharmacia Fine Chemicals) so that the extracted components were adsorbed thereon. The column was eluted with 800 ml of water and the obtained fraction was concentrated to dryness under reduced pressure to give 800 mg of dry concentrate of the extract fraction containing non-aconitine type alkaloidal components.

Purity Test

The same procedure as in the purity test described in Example 1 was followed to find no orange color spots.

EXAMPLE 19

Aqueous extract was obtained by following the same procedure as in Example 17 ①. 1 g of the aqueous extract was suspended in 1 ml of methanol arid was loaded onto a column packed with 100 g of alumina so that the extracted components were adsorbed thereon. The column was washed with 400 ml of chloroform/methanol (4:1) and then eluted with 300 ml of chloroform/methanol/water (12:10:3). The obtained fraction was concentrated to dryness under reduced pressure to give 25 mg of dry concentrate of the extract fraction containing non-aconitine type alkaloidal components.

Purity Test

The same procedure as in the purity test described in Example 1 was followed to find no orange color spots.

EXAMPLE 20

Aqueous extract was obtained by following the same procedure as in Example 17 ①. After 0.2 g of the aqueous extract was suspended in 0.5 ml of methanol, the suspension was loaded onto a column packed with 20 g of silica gel so that the extracted components were adsorbed thereon. The column was washed with 300 ml of chloroform/methanol/ammonia water (50:10:1) and then eluted with 150 ml of chloroform/methanol/water (6:4:1). The obtained fraction was concentrated to dryness under reduced pressure to give 19 mg of dry concentrate of the extract fraction containing non-aconitine type alkaloidal components.

Purity Test

The same procedure as in the purity test described in Example 1 was followed to find no orange color spots.

EXAMPLE 21

Aqueous extract was obtained by following the same procedure as in Example 17 ①. After 0.4 g of the aqueous extract was suspended in 0.5 ml of 50% methanol, the suspension was loaded onto a column packed with 70 ml of Toyopearl HW 40 F so that the extracted components were adsorbed thereon. The column was washed with 45 ml of 50% methanol and then eluted with 120 ml of 50% methanol. The obtained fraction was concentrated to dryness under reduced pressure to give 100 mg of dry concentrate of the extract fraction containing non-aconitine type alkaloidal components.

Purity Test

The same procedure as in the purity test described in Example 1 was followed to find no orange color spots.

EXAMPLE 22

To 100 g of finely divided Aconitum roots, 1 l of water was added to effect extraction under heating at about 100° C. for 1.5 hours. After the extract was allowed to cool at room temperature, it was centrifuged. The supernatant was loaded onto a column packed with 150 g of polyamide so that the extracted components were adsorbed thereon. After this column was washed with 2 l of water, it was eluted with 2 l of ethanol made alkaline with 3% ammonia. The eluate was concentrated to dryness under reduced pressure to give 1.6 g of dry concentrate of the extract fraction containing non-aconitine type alkaloidal components.

Purity Test

The same procedure as in the purity test described in Example 1 was followed to find no orange color spots.

EXAMPLE 23

To 100 g of finely divided Aconitum roots, 1 l of water was added to effect extraction under heating at about 100° C. for 1.5 hours. After the extract was allowed to cool at room temperature, it was centrifuged. The supernatant was loaded onto a column packed with 150 g of activated charcoal so that the extracted components were adsorbed thereon. The column was washed with 5 l of 20% methanol and then eluted with 4.5 l of methanol made alkline with 3% ammonia. The eluate was concentrated to dryness under reduced pressure to give 2.9 g of dry concentrate of the extract fraction containing non-aconitine type alkaloidal components.

Purity Test

The same procedure as in the purity test described in Example 1 was followed to find no orange color spots.

EXAMPLE 24

① To 100 g of finely divided Aconitum roots, 1 l of water was added to effect extraction under heating at about 100° C. for 1.5 hours. After the extract was allowed to cool at room temperature, it was centrifuged. The supernatant was concentrated to dryness under reduced pressure to give aqueous extract.

② After 4 g of the aqueous extract was suspended in 100 ml of 1N ammonia water, it was washed 5 times with 100 ml of ether. To the aqueous layer, 17 ml of 10N hydrochloric acid was added and the mixture was extracted 2 times with 100 ml of n-butanol. After the extract was washed 5 times with 20 ml of 1N hydrochloric acid, it was concentrated to dryness under reduced pressure to give 197 mg of dry concentrate of the extract fraction containing non-aconitine type alkaloidal components.

Purity Test

The same procedure as in the purity test described in Example 1 was followed to find no orange color spots.

EXAMPLE 25

To 100 g of finely divided Aconitum roots, 1 l of water was added to effect extraction under heating at about 100° C. for 1.5 hours. After-the extract was allowed to cool at room temperature, it was centrifuged. The supernatant was loaded onto a column packed with 80 g of CM-Sephadex C-25 (Pharmacia Fine Chemicals) so that the extracted components were adsorbed thereon. The column was eluted with 800 ml of water and the obtained fraction was concentrated to dryness under reduced pressure to give 795 mg of dry concentrate of the extract fraction containing non-aconitine type alkaloidal components.

Purity Test

The same procedure as in the purity test described in Example 1 was followed to find no orange color spots.

EXAMPLE 26

Aqueous extract was obtained by following the same procedure as in Example 24 (1). 1 g of the aqueous extract was suspended in 1 ml of methanol and the suspension was loaded onto a column packed with 100 g of alumina so that the extracted components were adsorbed thereon. The column was washed with 400 ml of chloroform methanol (4:1) and then eluted with 300 ml of chloroform/methanol/water (12:10:3). The obtained fraction was concentrated to dryness under reduced pressure to give 25 mg of dry concentrate of the extract fraction containing non-aconitine type alkaloidal components.

Purity Test

The same procedure as in the purity test described in Example 1 was followed to find no orange color spots.

EXAMPLE 27

Aqueous extract was obtained by following the same procedure as in Example 24 (1). After 0.2 g of the aqueous extract was suspended in 0.5 ml of methanol, it was loaded onto a column packed with 20 g of silica Eel so that the extracted components were adsorbed thereon. The column was washed with 300 ml of chloroform-/methanol/ammonia water (50:10:1) and then eluted with 150 ml of chloroform/methanol/water (6:4:1). The obtained fraction was concentrated to dryness under reduced pressure to give 20 mg of dry concentrate of the extract fraction containing non-aconitine type alkaloidal components.

Purity Test

The same procedure as in the purity test described in Example 1 was followed to find no orange color spots.

EXAMPLE 28

Aqueous extract was obtained by following the same procedure as in Example 24 (1). After 0.4 g of the aqueous extract was suspended in 0.5 ml of 50% methanol, it was loaded onto a column packed with 70 ml of Toyopearl HW 40 F so that the extracted components were adsorbed thereon. The column was washed with 45 ml of 50% methanol and then eluted with 120 ml of 50% methanol. The obtained fraction was concentrated to dryness under reduced pressure to give 105 mg of dry concentrate of the extract fraction, containing non-aconitine type alkaloidal components.

Purity Test

The same procedure as in the purity test described in Example 1 was followed to find no orange color spots.

In the following, the stimulative effect on hair growth and hair growing of the extract fraction containing non-aconitine type alkaloidal components used in the hair growth stimulant according to this invention will be demonstrated. The aqueous or ethanolic extract used in the experiments mentioned below was prepared in accordance with the following:

Preparation of Ethanolic Extract of Aconitum Roots 1 kg of ground Aconitum roots was extracted with 10 l of ethanol by refluxing for about 1.5 hours under heating. The extract was filtered and the filtrate was then concentrated to dryness under reduced pressure to give 140 g of ethanolic extract.

Preparation of Aqueous Extract of Aconitum Roots 1 kg of ground Aconitum roots was extracted with 10 l of water by heating at about 100° C. for 1.5 hours. The extract was filtered with a filter made of stainless (a net of about 0.246 mm meshes) by means of centrifugation (1350 revolutions per minute). The filtrate was concentrated to dryness to give 350 g of aqueous extract.

Experiment 1

In this experiment, male mice of Std:ddY strain (body weight 30–35 g) were used in groups of 7 each. The animals were maintained at 24°–25° C. of room temperature on a 12 h light–12 h dark cycle and were given food and water ad libitum. On the day before beginning of the experiment, the back of each mouse was shaved by a creamy hair remover. 0.1 g of each sample was dissolved in 20 ml of 60% ethanol and this solution was regarded as a sample solution. About 0.1 ml of the sample solution was applied to the hair-removed back, twice a day, i.e. in the morning and evening. To the negative control, 60% ethanol alone was applied as a sample. Judgement was made by means of macroscopic observation and the standard of judgement was as follows:

| Standard of judgement | score |
| --- | --- |
| Remarkable difference from negative control was observed | 3 |
| Distinct difference from negative control was observed | 2 |
| Difference from negative control was observed | 1 |
| Difference from negative control was not observed | 0 |

Results are shown in Table 3. From Table 3, it was demonstrated that the extract fraction of Aconitum roots which contains non-aconitine alkaloidal components and is used in the hair growth stimulant of this invention showed by far the better stimulative effect on hair growth and hair growing than the simple aqueous or alcoholic extract. Additionally, in the course of experiment and after the end of experiment, skin irritation or allergic reaction was not obserbed at all in groups to which the sample solution of the extract fraction containing non-aconitine type alkaloidal components mentioned-above was applied.

TABLE 3

| Sample | Score (mean) 21 day | Score (mean) 28 day |
| --- | --- | --- |
| Ethanolic extract from Aconitum roots | 1.8 | 2.0 |
| Aqueous extract from Aconitum roots | 2.0 | 2.3 |
| Dry concentrate of the extract fraction containing non-aconitine type alkaloidal components obtained in Example 1 | 2.4 | 2.8 |
| Dry concentrate of the extract fraction containing non-aconitine type alkaloidal components obtained in Example 2 | 2.6 | 2.8 |
| Dry concentrate of the extract fraction containing non-aconitine type alkaloidal components obtained in Example 3 | 2.4 | 2.6 |
| Dry concentrate of the extract fraction containing non-aconitine type alkaloidal components obtained in Example 8 | 2.4 | 2.7 |
| Dry concentrate of the extract fraction containing non-aconitine type alkaloidal components obtained in Example 9 | 2.5 | 2.8 |
| Dry concentrate of the extract fraction containing non-aconitine type alkaloidal components obtained in Example 10 | 2.7 | 2.7 |

TABLE 3-continued

| Sample | Score (mean) 21 day | 28 day |
|---|---|---|
| Dry concentrate of the extract fraction containing non-aconitine type alkaloidal components obtained in Example 15 | 2.5 | 2.8 |
| Dry concentrate of the extract fraction containing non-aconitine type alkaloidal components obtained in Example 16 | 2.6 | 2.9 |
| Dry concentrate of the extract fraction containing non-aconitine type alkaloidal components obtained in Example 17 | 2.6 | 2.6 |
| Dry concentrate of the extract fraction containing non-aconitine type alkaloidal components obtained in Example 22 | 2.4 | 2.6 |
| Dry concentrate of the extract fraction containing non-aconitine type alkaloidal components obtained in Example 23 | 2.5 | 2.7 |
| Dry concentrate of the extract fraction containing non-aconitine type alkaloidal components obtained in Example 24 | 2.7 | 2.8 |

In this experiment, male mice of Std:ddY strain (body weight 30–35 g) were used in groups of 7 each. The animals were maintained at 24°–25° C. of room temerature on a 12 h light–12 h dark cycle and were given food and water ad libitum. On the day before beginning of the experiment, the back of each mouse was shaved by a creamy hair remover. The same sample solution as in Experiment 1 was used. About 0.1 ml of the sample solution was applied to the hair-removed back, twice a day, i.e. in the morning and evening. On 21st day and 28th day after sample application, newly generated hair on from the site of hair removal was sampled (picked up) and the length thereof measured by means of a stereomicroscope. 5 longer ones out of randomly chosen 20 sampled hairs were identified and the mean value of the length of these 5 hairs was regarded as the body hair length of mouse. To evaluate the significance of differences for drug-administered groups based on comparison between groups, Student's t-test was conducted. The results are shown in Table 4. As can be seen From Table 4, the extract fraction containing non-aconitine type alkaloidal components of Aconitum roots showed a significant (P<0.01) stimulative effect on hair growth and hair growing, in comparison with negative control or simple aqueous or ethanolic extract.

TABLE 4

| Sample | body hair length (mm, mean ± standard error) 21st day | 28th day |
|---|---|---|
| Negative control | 6.66 ± 0.18 | 7.59 ± 0.17 |
| Ethanolic extract from Aconitum roots | 7.16 ± 0.08* | 8.34 ± 0.09** |
| Aqueous extract from Aconitum roots | 7.20 ± 0.08* | 8.27 ± 0.09** |
| Dry concentrate of the extract fraction containing non-aconitine type alkaloidal components obtained in Example 1 | 7.86 ± 0.16**† | 9.30 ± 0.25**† |
| Dry concentrate of the extract fraction containing non-aconitine type alkaloidal components obtained in Example 2 | 8.17 ± 0.19**† | 9.13 ± 0.18**† |
| Dry concentrate of the extract fraction containing non-aconitine type alkaloidal components obtained in Example 3 | 7.91 ± 0.09** | 9.22 ± 0.21** |
| Dry concentrate of the extract fraction containing non-aconitine type alkaloidal components obtained in Example 8 | 8.00 ± 0.16**† | 8.94 ± 0.16**† |
| Dry concentrate of the extract fraction containing non-aconitine type alkaloidal components obtained in Example 9 | 7.93 ± 0.08** | 9.14 ± 0.10** |
| Dry concentrate of the extract fraction containing non-aconitine type alkaloidal components obtained in Example 10 | 8.14 ± 0.14** | 9.08 ± 0.15** |
| Dry concentrate of the extract fraction containing non-aconitine type alkaloidal components obtained in Example 15 | 8.36 ± 0.07** | 9.27 ± 0.08** |
| Dry concentrate of the extract fraction containing non-aconitine type alkaloidal components obtained in Example 16 | 7.89 ± 0.09** | 8.96 ± 0.09** |
| Dry concentrate of the extract fraction containing non-aconitine type alkaloidal components obtained in Example 17 | 8.25 ± 0.17** | 9.10 ± 0.13** |
| Dry concentrate of the extract fraction containing non-aconitine type alkaloidal components obtained in Example 22 | 8.06 ± 0.07** | 9.03 ± 0.08** |
| Dry concentrate of the extract fraction containing non-aconitine type alkaloidal components obtained in Example 23 | 8.18 ± 0.12** | 9.29 ± 0.21** |
| Dry concentrate of the extract fraction containing non-aconitine type alkaloidal components obtained in Example 24 | 8.15 ± 0.16** | 9.12 ± 0.11** |

*$P<0.05$, ** $P<0.01$: comparison with negative control group.
†$P<0.01$: comparison with aqueous and ethanolic extracts of Aconitum roots.

Next, experimental examples on pharmacological action of the fraction containing non-aconitine type alkaloidal components of Aconitum roots used in the blood circulation stimulant according to this invention are shown.

Experiment 3

Blood Flow Increasing Effect

In this experiment, male mice of Std:ddY strain (20~25 g) were used in groups of 5 each. The animals were maintained at 24°–25° C. of room temperature on a 12 h light–12 h dark cycle and were given food and water ad libitum. An appropriate amount of each sample was dissolved in dimethyl sulfoxide. On the day before beginning of the experiment, the back of mouse was shaved with a creamy hair remover. After anesthetized with urethane, the probe of a Laser Doppler Flow meter (ALF 21, product of Advance) was attached onto the hair-removed back of mouse. Before administration of the sample solution, the blood flow was measured. 0.05 ml of the sample solution was then injected into the animal's tail vein. After 10 rain, the blood flow (in ml/min/100 g) was measured for 25 min. Results were indicated in terms of the accumulated blood flow increase over a period of 25 minutes from 10 minutes after the sample administration, in comparison with the blood flow before the sample administration. Negative control group was given only dimethylsulfoxide. To evaluate the significance of differences for drug-administered groups based on comparison between groups, Student's t-test was conducted. Results are shown in Table 5. As can be seen from Table 5, the extract fraction containing non-aconitine type alkaloidal components of Aconitum roots mentioned above showed significant ($P < 0.01$) stimulative effect on blood flow, in comparison with negative control group.

TABLE 5

| Sample | Dose (mg/mouse) | mean ± standard error (ml) |
|---|---|---|
| Negative control | 0 | 1.2 ± 1.0 |
| Dry concentrate of the extract fraction containing non-aconitine type alkaloidal components obtained in Example 1 | 0.05 | 16.3 ± 2.4(*) |
| Dry concentrate of the extract fraction containing non-aconitine type alkaloidal components obtained in Example 2 | 0.05 | 14.9 ± 3.8(*) |
| Dry concentrate of the extract fraction containing non-aconitine type alkaloidal components obtained in Example 3 | 0.05 | 15.2 ± 3.5(*) |
| Dry concentrate of the extract fraction containing non-aconitine type alkaloidal components obtained in Example 8 | 0.05 | 15.1 ± 3.3(*) |
| Dry concentrate of the extract fraction containing non-aconitine type alkaloidal components obtained in Example 9 | 0.05 | 17.0 ± 5.2(*) |
| Dry concentrate of the extract fraction containing non-aconitine type alkaloidal components obtained in Example 10 | 0.05 | 15.4 ± 4.3(*) |
| Dry concentrate of the extract fraction containing non-aconitine type alkaloidal components obtained in Example 15 | 0.05 | 15.9 ± 3.6(*) |
| Dry concentrate of the extract fraction containing non-aconitine type alkaloidal components obtained in Example 16 | 0.05 | 14.5 ± 2.2(*) |
| Dry concentrate of the extract fraction containing non-aconitine type alkaloidal components obtained in Example 17 | 0.05 | 17.2 ± 4.8(*) |
| Dry concentrate of the extract fraction containing non-aconitine type alkaloidal components obtained in Example 22 | 0.05 | 15.8 ± 5.5(*) |
| Dry concentrate of the extract fraction containing non-aconitine type alkaloidal components obtained in Example 23 | 0.05 | 14.6 ± 3.4(*) |
| Dry concentrate of the extract fraction containing non-aconitine type alkaloidal components obtained in Example 24 | 0.05 | 16.6 ± 4.9(*) |

*$P < 0.01$

Experiment 4

Blood Flow Increasing Effect

An ointment was prepared on the basis of Formulation 1 using the fraction containing non-aconitine type alkaloidal components of Aconitum roots obtained in Example 1. Male adults of human beings were adopted as test subjects and the blood flow was measured. Test condition was as described in the following: The test subject was laid in supine position and the probe of a Laser Doppler Flow meter (ALF21, product of Advance) was attached onto the back of his hand. The blood flow before the application of the ointment was measured for about 30 minutes. Next, the abovementioned ointment was applied around the attached probe and the blood flow was measured for about one hour. Results was given in terms of minimum and maximum blood flows reached during 30 minutes before, as well as during 15 min to 1 hour after, the ointment application. The results are shown in Table 6. As shown in Table 6, by the application of the ointment with the extract fraction containing non-aconitine type alkaloidal components of Aconitum roots, remarkable increases in blood flow were obserbed.

TABLE 6

| | before ointment application | after ointment application |
|---|---|---|
| Minimum blood flow (ml/min/100 g) | 3.2 | 4.3 |
| Maximum blood flow (ml/min/100 g) | 4.0 | 5.3 |

In the following will now be shown results on acute toxicity and safety of the extract fraction containing non-aconitine type alkaloidal components of Aconitum roots.

Experiment 5

Acute Toxicity

In this experiment, male mice of Std:ddY strain (20–25 g) were used. An appropriate amount of each sample was suspended in water and the suspension was administered p.o. at the dose shown in Table 7. The mortality during 72 hours after administration was determined. The results are shown in Table 7. As shown in Table 7, no death of mice was seen even at the p.o. administration of 3 g/kg of the extract fraction containing non-aconitine type: alkaloidal components of Aconitum roots of this invention, which was thus found to be by far lower in toxicity than the simple extracts of Aconitum roots with water or ethanol.

TABLE 7

| Sample | Dose (g/kg) | mortality |
|---|---|---|
| Ethanolic extract from Aconitum roots | 1 | 5/5 |
| Aqueous extract from Aconitum roots | 1 | 5/5 |
| Dry concentrate of the extract fraction containing non-aconitine type alkaloidal components obtained in Example 1 | 3 | 0/8 |
| Dry concentrate of the extract fraction containing non-aconitine type alkaloidal components obtained in Example 2 | 3 | 0/8 |
| Dry concentrate of the extract fraction containing non-aconitine type alkaloidal components obtained in Example 3 | 3 | 0/8 |
| Dry concentrate of the extract fraction containing non-aconitine type alkaloidal components obtained in Example 8 | .3 | 0/8 |
| Dry concentrate of the extract fraction containing non-aconitine type alkaloidal components obtained in Example 9 | 3 | 0/8 |
| Dry concentrate of the extract fraction containing non-aconitine type alkaloidal components obtained in Example 10 | 3 | 0/8 |
| Dry concentrate of the extract fraction containing non-aconitine | 3 | 0/8 |

TABLE 7-continued

| Sample | Dose (g/kg) | mortality |
|---|---|---|
| type alkaloidal components obtained in Example 15 | | |
| Dry concentrate of the extract fraction containing non-aconitine type alkaloidal components obtained in Example 16 | 3 | 0/8 |
| Dry concentrate of the extract fraction containing non-aconitine type alkaloidal components obtained in Example 17 | 3 | 0/8 |
| Dry concentrate of the extract fraction containing non-aconitine type alkaloidal components obtained in Example 22 | 3 | 0/8 |
| Dry concentrate of the extract fraction containing non-aconitine type alkaloidal components obtained in Example 23 | 3 | 0/8 |
| Dry concentrate of the extract fraction containing non-aconitine type alkaloidal components obtained in Example 24 | 3 | 0/8 |

Experiment 6

Safety

As the test method, a 24-hour patch test on human forearm was used. Test subjects consisted of 3 male and 1 female adults. The judgement was based on the standard shown below. The sample used was prepared in accordance with Formulation 1 using the extract fraction containing non-aconitine type alkaloidal components of Aconitum roots.

| | | | |
|---|---|---|---|
| ++: Severe erythema | | ±: Slight erythema | |
| +: Erytheam | | −: Negative | |

The results are shown in Table 8. As shown in Table 8, skin irritation and allergic reaction to this sample were not seen at all, demonstrating that the safety of this sample was very high. Additionally, during the test, no side effects were observed with the subjects.

TABLE 8

| Judgement | number |
|---|---|
| ++ | 0 |
| + | 0 |
| ± | 0 |
| − | 4 |

In the following will now be given examples of formulation for the hair growth stimulant according to this invention.

| [Formulation 1] hair tonic | |
|---|---|
| ethanol | 60 ml |
| propylene glycol | 3 g |
| the dry concentrate of the extract fraction containing non-aconitine type alkaloidal components obtained in Example 1 | 1 g |
| perfume | proper quantity |

Total volume was made up to 100 ml by addition of purified water.

| [Formulation 2] hair lotion | |
|---|---|
| ethanol | 2 g |

| [Formulation 2] hair lotion | |
|---|---|
| glycerin | 0.5 g |
| isopropylmethylphenol | 0.4 g |
| resorsin | 2 g |
| l-menthol | 1 g |
| the dry concentrate of the extract fraction containing non-aconitine type alkaloidal components obtained in Example 1 | 1 g |
| perfume | proper quantity |

Total volume was made up to 100 ml by addition of purified water.

| [Formulation 3] hair cream | |
|---|---|
| (A) Oil phase components were prepared in accordance with the following formulation: | |
| liquid paraffin | 40 g |
| white beeswax | 2.5 g |
| polyoxyethylene stearyl ether (20 E.O.) | 1.5 g |
| polyoxyethylene stearyl ether (5 E.O.) | 3.0 g |
| sorbitan monostearate | 1.5 g |
| the dry concentrate of the extract fraction containing non-aconitine type alkaloidal components obtained in Example 1 | 1 g |
| (B) Water phase components were prepared in accordance with the following formulation: | |
| sodium borate | 0.4 g |
| tetrasodium edetate | 1 g |
| propylene glycol | 5 g |
| purified water proper quantity (sufficient for the total volume to be made up to 100 ml) | |

Oil phase components (A) and water phase components (B) were heated up to 75° C. and 77° C., respectively, with stirring. While stirring, (B) was slowly added to (A) to give an emulsion.

| [Formulation 4] hair shampoo | |
|---|---|
| Components (A) | |
| triethanolamine lauryl ether sulfate | 15 g |
| coconut fatty acid diethanolamide | 5 g |
| ethyleneglycol monostearate | 2 g |
| Components (B) | |
| the dry concentrate of the extract fraction containing non-aconitine type alkaloidal components obtained in Example 1 | 1 g |
| sodium lauryl sulfate | 5 g |
| purified water proper quantity (sufficient for the total volume to be made up to 100 ml) | |

After components (A) and (B) were separately heated and stirred, components (B) were slowly added to components (A) under stirring to give a solution for use as a shampoo.

In the following will now be given examples of formulation for the blood circulation stimulant according to this invention.

| [Formulation 1] ointoment | |
|---|---|
| white vaseline | 25 g |
| propylene glycol | 12 g |
| stearyl alcohol | 22 g |
| sodium lauryl sulfate | 1.5 g |
| the dry concentrate of the extract fraction containing non-aconitine type alkaloidal components obtained in Example 1 | 3 g |
| purified water | proper quantity |
| Total weight | 100 g |

| [Formulation 2] tablet (in 10 tablets) | |
| --- | --- |
| carboxymethyl cellulose | 0.8 g |
| calcium stearate | 0.02 g |
| magnesium aluminometasilicate | 0.03 g |
| the dry concentrate of the extract fraction containing non-aconitine type alkaloidal components obtained in Example 1 | 1 g |
| lactose | proper quantity |
| Total weight | 2.0 g |

| [Formulation 3] cream | |
| --- | --- |
| beeswax | 10 g |
| liquid paraffin | 50 g |
| sodium borate | 1 g |
| the dry concentrate of the extract fraction containing non-aconitine type alkaloidal components obtained in Example 1 | 1 g |
| purified water | proper quantity |
| Total weight | 100 g |

| [Formulation 4] suppositories | |
| --- | --- |
| glycerin | 91 g |
| sodium stearate | 9 g |
| the dry concentrate of the extract fraction containing non-aconitine type alkaloidal components obtained in Example 1 | 1 g |
| purified water | 5 g |
| Total weight | 106 g |

I claim:

1. A blood circulation stimulant composition consisting essentially of an extract fraction of aconitum roots containing non-aconitine alkaloidal components and substantially devoid of aconitine alkaloidal components optionally with a pharmaceutically acceptable carrier or diluent.

2. The composition of claim 1 containing from 0.05 to 10% weight of said extract.

3. A topical blood circulation stimulant composition consisting essentially of from 0.05 to 10% by weight of an extract fraction of aconitum roots containing non-aconitine alkaloidal components and substantially devoid of aconitine alkaloidal components together with a topically acceptable carrier or diluent.

4. The composition of claim 3 containing from 0.1 to 5% by weight of said extract.

5. A topical hair growth stimulant composition consisting essentially of from 0.05 to 10% by weight of an extract fraction of aconitum roots containing non-aconitine alkaloidal components and substantially devoid of aconitine alkaloidal components together with a topically acceptable carrier or diluent.

6. The composition of claim 5 containing form 0.1 to 5% by weight of said extract.

7. A composition consisting essentially of aconitum roots containing non-aconitine alkaloidal components and substantially devoid of aconitine alkaloidal components.

8. A composition consisting essentially of an extract fraction of aconitum roots containing non-aconitine alkaloidal components and substantially devoid of aconitine alkaloidal components, said composition prepared by the process comprising:
  (a) extracting aconitum roots with water or alcohol, and
  (b) separating the resistant aqueous or alcoholic extract by mass partition between the solid-liquid phases or liquid-liquid phases to remove aconitine alkaloidal components.

* * * * *